United States Patent [19]

Hoelderich et al.

[11] Patent Number: 5,225,602
[45] Date of Patent: * Jul. 6, 1993

[54] PHENYLACETALDEHYDES AND THE PREPARATION OF PHENYLACETALDEHYDES

[75] Inventors: Wolfgang Hoelderich, Frankenthal; Norbert Goetz, Worms; Leopold Hupfer, Friedelsheim; Rudolf Kropp; Hans Theobald, both of Limburgerhof; Bernd Wolf, Mutterstadt, all of Fed. Rep. of Germany

[73] Assignee: BASF Aktiengesellschaft, Ludwigshafen, Fed. Rep. of Germany

[*] Notice: The portion of the term of this patent subsequent to May 29, 2007 has been disclaimed.

[21] Appl. No.: 425,372

[22] Filed: Oct. 17, 1989

Related U.S. Application Data

[63] Continuation of Ser. No. 213,477, Jun. 30, 1988, abandoned, which is a continuation of Ser. No. 944,518, Dec. 22, 1986, abandoned.

[30] Foreign Application Priority Data

Dec. 11, 1985 [DE] Fed. Rep. of Germany ....... 3546372

[51] Int. Cl.$^5$ .................. C07C 315/00; C07C 47/52; C07C 47/54; C07C 47/542
[52] U.S. Cl. .................................. 568/41; 568/425; 568/426; 568/427; 568/437; 568/477; 568/442
[58] Field of Search ............... 568/41, 425, 427, 437, 568/426, 447, 442

[56] References Cited

U.S. PATENT DOCUMENTS

| 2,444,400 | 6/1948 | Emerson | 568/426 |
| 2,628,255 | 2/1953 | Sexton et al. | 568/427 |
| 3,845,076 | 10/1974 | Tsuchihashi et al. | 568/425 X |
| 4,495,371 | 1/1985 | Neri et al. | 568/427 |
| 4,929,765 | 5/1990 | Smuda et al. | |
| 4,980,511 | 12/1990 | Hoelderich et al. | 568/427 |

FOREIGN PATENT DOCUMENTS

| 0100117 | 7/1983 | European Pat. Off. | |
| 51233 | 5/1974 | Japan | 568/426 |
| 112040 | 5/1986 | Japan | 568/427 |

OTHER PUBLICATIONS

Ullmann's Encyclopedia, 1983, pp. 575–577.
Kugita et al., Chem. Pharm. Bull. 18(10) 2028–2037 (1970).
Patent Abstracts of Japan, vol. 10, No. 350. (C–387) (2406) Nov. 26, 1986.

*Primary Examiner*—José G. Dees
*Assistant Examiner*—Joseph Conrad, III
*Attorney, Agent, or Firm*—Keil & Weinkauf

[57] ABSTRACT

Phenylacetaldehydes of the structure (I)

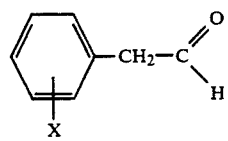

where the substituents X are 2,4-dichloro, difluoro, trifluoro, tetrafluoro, p-trifluoromethyl, 2-methyl-4-fluoro, haloalkoxy or haloalkylthio radicals or are adjacent Cl, F, $CF_3$, alkyl, alkoxy, haloalkoxy and/or haloalkylthio radicals.

6 Claims, No Drawings

PHENYLACETALDEHYDES AND THE PREPARATION OF PHENYLACETALDEHYDES

This application is a continuation of application Ser. No. 213,477, filed on Jun. 30, 1988 which is a continuation of application Ser. No. 944,518, filed on Dec. 22, 1986 now abandoned.

The present invention relates to novel substituted phenylacetaldehydes which are useful intermediates for the preparation of novel active ingredients for insecticides. The application furthermore relates to a process for the preparation of these phenylacetaldehydes.

Known processes for the preparation of phenylacetaldehydes which can also be carried out on an industrial scale are: a) The dehydration of phenylethanols: Only partial conversion is possible; separation of the starting material and end product entails large losses (phenylacetaldehydes are thermally unstable); formation of autocondensation products during fractionation.

Halogen-containing phenylacetaldehydes cannot be prepared by this route since elimination of halogen takes place under the reaction conditions. b) The rearrangement of styrene oxides: As a rule, only partial conversion in this case too; by-products difficult to separate off; poor selectivities; poor lives of the catalysts used to date, because of coating of the surface.

European Patent 100,117 describes the reaction of styrene oxide and of styrene oxides which are alkyl-substituted or alkoxy-substituted in the aromatic nucleus over a titanium-containing zeolite at from 30° to 100° C. in the liquid phase to give β-phenylaldehydes. The catalyst used for this purpose has to be produced by a complicated process from expensive, very pure educts, such as tetraalkyl orthosilicates, tetraalkyl orthotitanates and tetrapropylammonium hydroxide. High conversion is achieved only if the reaction takes place in a solvent such as methanol or acetone at from 30° to 100° C. in the liquid phase, and residence times of from 1 to 1.5 hours are maintained. This entails higher distillation and operating costs. Furthermore, the reaction over the titanium-containing zeolites is not universally applicable and is only possible in the case of styrene oxide and styrene oxides which are alkylated or alkoxylated in the aromatic moiety.

Other work on the rearrangement of epoxides to give carbonyl compounds is known. For example, cyclododecanone is obtained from epoxycyclododecane, over Pd-doped or Rd-doped $Al_2O_3$. In this work, it is expressly pointed out that zeolites are unsuitable for this reaction. The use of A zeolites for the rearrangement of butylene oxide to butyraldehyde (from 55 to 72%) have also been described. The selectivity is unsatisfactory. Furthermore, the A zeolite catalyst is difficult to regenerate after it has been deactivated by coking, since the crystal structure of the zeolite is destroyed at the temperature of about 500° C. which is required for this purpose. Moreover, the conversion of propylene oxide to acetone or propionaldehyde over alkali metal-doped X zeolites has to be carried out in the presence of strongly acidic centers.

It is also known that phenylacetaldehydes can be obtained by rearrangement of styrene glycol over aluminum silicates containing 80:20-93:7 of $SiO_2:Al_2O_3$ mixed with, for example, iron oxide, calcium oxide or magnesium oxide, or over activated clay, in suspension under reduced pressure. These two processes have in common the fact that the yields are unsatisfactory, being 50-86%. Furthermore, no information is given regarding the life and regeneratability of the catalysts. This process too is not versatile, and halogenated compounds are not obtained. The clay used is a natural mineral which, depending on the source, has a different composition and hence different catalytic properties and selectivity. This presents problems, particularly in a continuous industrial process.

Aldehydes can also be obtained by subjecting carbonyl chlorides to a Rosenmund reduction. Reactions of this type take place smoothly in the liquid phase in the case of aryl acid chlorides. In the case of other acid chlorides, e.g. aralkylcarbonyl chlorides, lower yields coupled with poisoning of the catalyst are generally encountered.

The present invention relates to phenylacetaldehydes of the structure (I)

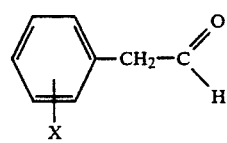

where the substituents X are 2,4-dichloro, difluoro, trifluoro, tetrafluoro, p-trifluoromethyl, 2-methyl-4-fluoro, haloalkoxy or haloalkylthio or are adjacent Cl, F, $CF_3$, alkyl, alkoxy, haloalkoxy and/or haloalkylthio radicals.

The present invention furthermore relates to processes for the preparation of the phenylacetaldehydes of the structure (I) from readily available starting materials in the presence of a catalyst which is readily available, possesses high activity and can easily be regenerated. Moreover, long catalyst lives coupled with high conversions, high selectivities and versatility of the catalyst with regard to the educts are ensured.

In the novel process, the disadvantages mentioned at the outset, of the previous procedures, are overcome, and the requirements set in respect of catalysts are met. In view of the prior art, the success of the process is all the more surprising since to date only weakly acidic X zeolites have been used and zeolites were regarded as unsuitable for rearrangement reactions. It was therefore not to be expected that such excellent results would be obtained, within such wide limits and with such a wide variety of educts, precisely with the zeolites which possess high acidity and strictly defined structural parameters.

The advantages of the novel process for the rearrangement over the catalyst according to the invention are complete conversion, no separation problems, long lives, selectivities >90%, very good yields for halogen-containing starting materials too, simple isolation of the end products, as a rule re-use without additional purification, and easy regeneration of the catalysts in the event of coking. The Rosenmund reduction has been important to date only for the hydrogenation of aromatic carbonyl chlorides to give benzaldehydes; it is surprising that even sensitive halogen-containing phenylacetaldehydes can be prepared by this method. The crude products obtained can be further processed directly, the starting materials are readily available and poisoning of the catalyst is not observed in the case of the catalyst according to the invention.

The processes according to the invention are:

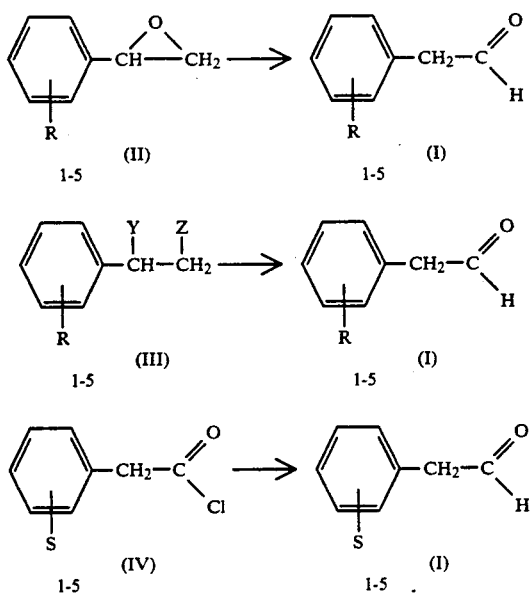

R may be hydrogen, alkyl, alkoxy, halogen, haloalkyl, haloalkoxy and/or haloalkylthio, Y and Z may be identical or different and are each hydroxyl, alkoxy, aryloxy or acyloxy, and S may be halogen, haloalkyl, haloalkoxy and/or haloalkylthio.

Examples of epoxides used for the novel process are styrene oxide, p-fluorostyrene oxide, p-chlorostyrene oxide, 2,4-difluorostyrene oxide, 3,4-difluorostyrene oxide, 2,4-dichlorostyrene oxide, 2,4,5-trifluorostyrene oxide, o-, m- and p-trifluoromethylstyrene oxide, o-, m- and p-methylstyrene oxide, o-, m- and p-methoxystyrene oxide, 2,3,4,5-tetrafluorostyrene oxide, p-trifluoromethoxystyrene oxide, p-trifluoromethylthiostyrene oxide, 2-fluoro-6-chlorostyrene oxide, 2-fluoro-4-trifluoromethylstyrene oxide, 2-fluoro-4-trifluoromethoxystyrene oxide and 2-methyl-4-fluorostyrene oxide.

Examples of phenylglycols used for the novel process are phenylglycol, phenylglycol monomethyl ether, phenyl glycolacetate and phenylglycol monophenyl ether.

Examples of aromatic carbonyl chlorides used for the novel process are o-, m- and p-phenylacetyl chloride, o-, m- and p-fluorophenylacetyl chloride, 2-chloro-6-fluorophenylacetyl chloride and o-, m- and p-trifluoromethylphenylacetyl chloride.

The abovementioned compounds represent a selection of components which can be used for the preparation of substituted phenylacetaldehydes and is not intended to restrict the range of application of the novel process, which can be used for a large number of phenylacetaldehydes.

The catalysts used for the novel conversion of epoxides are acidic zeolite catalysts. Zeolites are crystalline aluminosilicates which have a highly ordered structure with a rigid three-dimensional network of $SiO_4$ and $AlO_4$ tetrahedra which are connected by common oxygen atoms. The ratio of Si and Al atoms to oxygen is 1:2 (cf. Ullmanns Encyklopädie der techn. Chemie. 4th edition, volume 24, page 575 (1983)). The electrovalency of the aluminum-containing tetrahedra is compensated by the inclusion of cations in the crystal, for example an alkali metal or hydrogen ion. Cation exchange is possible. The voids between the tetrahedra are occupied by water molecules prior to dehydration by drying or calcination.

In the zeolites, it is also possible, instead of aluminum, to incorporate other elements, such as B, Ga, Fe, Cr, Be, As or Sb, into the lattice, or to replace the silicon with a tetravalent element, such as Ge.

Suitable catalysts are zeolites from the mordenite group or fine-pore zeolites of the erionite or chabazite type. Zeolites of the pentasil type are particularly advantageous for the process according to the invention. The zeolites can have different chemical compositions. They are aluminosilicate, borosilicate, iron silicate, gallium silicate, chromium silicate, berylium silicate, arsenosilicate, antimony silicate and bismuth silicate zeolites and mixtures of these, as well as aluminogermanate, borogermanate, gallium germanate and iron germanate zeolites and mixtures of these.

The aluminosilicate, borosilicate and iron silicate zeolites of the pentasil type are particularly useful for the novel process. The aluminosilicate zeolite is prepared, for example, from an aluminum compound, preferably $Al(OH)_3$ or $Al_2(SO_4)_3$, and a silicon component, preferably finely divided silica, in an aqueous solution of an amine or polyamine, in particular in 1,6-hexanediamine, 1,3-propanediamine or triethylenetetramine solution, with or, in particular, without the addition of an alkali metal or alkaline earth metal, at from 100° to 220° C. under autogenous pressure. The isotactic zeolites according to German Laid-Open Application DOS 3,006,471 are also included here. The resulting aluminosilicate zeolites have an $SiO_2/Al_2O_3$ ratio of from 10 to 40,000, depending on the amounts of starting materials chosen. Aluminosilicate zeolites of this type can also be synthesised in an ether medium, such as diethylene glycol dimethyl ether, in an alcoholic medium, such as methanol or butane-1,4-diol, or in water.

The borosilicate zeolite is synthesised, for example at from 90° to 200° C. under autogenous pressure, by reacting a boron compound, e.g. $H_3BO_3$, with a silicon compound, preferably finely divided silica, in an aqueous solution of an amine, in particular in 1,6-hexanediamine, 1,3-propanediamine or triethylenetetramine solution, with or, in particular, without the addition of an alkali metal or alkaline earth metal. The isotactic zeolites according to German Laid-Open Application DOS 3,006,471 are also included here. Such borosilicate zeolites can also be prepared if the reaction is carried out not in an aqueous solution of an amine but in an ether solution, e.g. diethylene glycol dimethyl ether, or in an alcoholic solution, e.g. hexane-1,6-diol.

The iron silicate zeolite is obtained, for example, from an iron compound, preferably $Fe_2(SO_4)_3$, and a silicon compound, preferably finely divided silica, in an aqueous solution of an amine, in particular 1,6-hexanediamine, with or without the addition of an alkali metal or alkaline earth metal, at from 100° to 220° C. under autogenous pressure.

The aluminosilicate, borosilicate and iron silicate zeolites prepared in this manner can be isolated, dried at from 100° to 160° C., preferably 110° C., calcined at from 450° to 550° C., preferably from 500° to 540° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried at 110° C. for 116 hours and calcined at 500° C. for 16 hours.

Advantageous catalysts are also obtained if the aluminosilicate or borosilicate zeolite isolated is molded directly after drying and is subjected to calcination only after the molding procedure. The aluminosilicate and borosilicate zeolites prepared can be used in pure form, without a binder, as extrudates or pellets, the extruding or peptization assistants used being, for example, ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but in, for example, the Na form, the latter can be converted partially or completely to the desired H form by ion exchange, for example with ammonium ions, followed by calcination, or by treatment with an acid.

If, when the zeolite catalysts are used according to the invention, any deactivation due to coking occurs, it is advisable to regenerate the zeolites by burning off the coke with air or with an air/$N_2$ mixture at from 400° to 550° C., preferably from 500° to 540° C. As a result, the zeolites regain their initial activity. By precoking, the activity of the catalyst can be adjusted to achieve optimum selectivity with respect to the desired reaction product.

In order to achieve very high selectivity, high conversion and long lives, it is sometimes advantageous to modify the catalysts. A suitable method for modifying the catalysts comprises, for example, doping the unmolded or molded zeolites with metal salts by ion exchange or impregnation.

Doping is advantageously carried out by a procedure in which, for example, the molded pentasil zeolite is initially taken in a riser tube and, for example, an aqueous or ammoniacal solution of a halide or of a nitrate of the metals is passed over at from 20° to 100° C. Ion exchange of this type can be carried out, for example, for the hydrogen, ammonium and alkali metal form of the zeolite. Another possible method of applying metal to the zeolite comprises impregnating the zeolite material, for example with a halide, a nitrate or an oxide of the metals, in aqueous, alcoholic or ammoniacal solution. Both ion exchange and impregnation are followed by one or more drying steps and, if desired, repeated calcination.

In a possible embodiment, for example, $Cs_2CO_3$ is dissolved in water, and the molded or unmolded zeolite is impregnated with this solution for a certain time (about 30 minutes). Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible, for example, to prepare an ammoniacal $Pd(NO_3)_2$ solution and to suspend the pure zeolite powder in this solution for about 24 hours at from 40° to 100° C., while stirring. After it has been filtered off, dried at about 150° C. and calcined at about 500° C., the zeolite material obtained in this manner can be further processed, with or without a binder, to extrudates, pellets or fluidizable material.

Ion exchange with the zeolite in the H form can be carried out as follows: the zeolites, in the form of extrudates or pellets, are initially taken in a column and, for example, an ammoniacal $Pd(NO_3)_2$ solution is circulated over the zeolite at slightly elevated temperatures of from 30° to 80° C. for from 15 to 20 hours. The zeolite is then washed thoroughly with water, dried at about 150° C. and calcined at about 550° C.

In the case of some metal-doped zeolites, after-treatment with hydrogen is advantageous.

In another possible method of modification, the molded or unmolded zeolite material is treated with an acid such as hydrochloric acid, hydrofluoric acid or phosphoric acid and/or steam.

Other catalysts for the preparation of phenylacetaldehydes from the corresponding epoxides or glycols are described below.

Aluminum phosphate catalysts used for the novel process are, in particular, aluminum phosphates synthesised under hydrothermal conditions.

Examples of these aluminum phosphates are APO-5, APO-9, APO-11, APO-12, APO-14, APO-21, APO-25, APO-31 and APO-33. Syntheses of these compounds are described in European Patent 132,708 and U.S. Pat. Nos. 4,310,440 and 4,473,663.

For example, $AlPO_4$-5 (APO-5) is synthesised by a procedure in which orthophosphoric acid is mixed with pseudoboehmite (Catapal SB®) in water to give a homogeneous mixture, tetrapropylammonium hydroxide is added to this mixture and the reaction is then carried out at about 150° C. for from 20 to 60 hours under autogenous pressure in an autoclave. The $AlPO_4$ filtered off is dried at from 100° to 160° C. and calcined at from 450° to 550° C.

$AlPO_4$-9 (APO-9) is likewise synthesised from orthophosphoric acid and pseudoboehmite but in an aqueous 1,4-diazabicyclo[2.2.2]octane (DABCO) solution at about 200° C. under autogenous pressure in the course of from 200 to 400 hours.

$AlPO_4$-21 (APO-21) is synthesised from orthophosphoric acid and pseudoboehmite in aqueous pyrrolidone solution at 150° to 200° C. under autogenous pressure in the course of from 50 to 200 hours.

The silicon aluminum phosphates used for the novel process are, for example, SAPO-5, SAPO-11, SAPO-31 and SAPO-34. The synthesis of this compound is described in, for example, European Patent 103,117 and U.S. Pat. No. 4,440,871. SAPOs are prepared by crystallization from an aqueous mixture at from 100° to 250° C. under autogenous pressure in the course of from 2 hours to 2 weeks, the reaction mixture consisting of a silicon, an aluminum and a phosphorous component being reacted in aqueous solutions containing organic amino compounds.

For example, SAPO-5 is obtained by mixing $SiO_2$, suspended in aqueous tetrapropylammonium hydroxide solution with an aqueous suspension of pseudoboehmite and orthophosphoric acid and then carrying out the reaction at from 150° to 200° C. in the course of from 20 to 200 hours under autogenous pressure in a stirred autoclave. The powder is filtered off, dried at from 110° to 160° C. and calcined at from 450° to 550° C.

Examples of suitable silicon aluminum phosphates are ZYT-5, ZYT-6, ZYT-7, ZYT-9, ZYT1-11 and ZYT-12 (J 5 9217-619).

Borophosphates for the novel process can be prepared, for example, by mixing and kneading concentrated boric acid and phosphoric acid and then drying and calcining the product in an inert gas, air or vapor atmosphere at from 250° to 650° C., preferably from 300° to 500° C.

Phosphoric acid or boric acid is applied to an $SiO_2$, $Al_2O_3$ or pumice carrier, for example by impregnation or spraying. The catalyst containing phosphoric acid can be obtained, for example, by impregnating $SiO_2$ with an $H_3PO_4$, $NaH_2PO_4$ or $Na2HPO_4$ solution and then drying and calcining the product. However, it is also possible for phosphoric acid to be sprayed together with silica gel into a spray tower and the product then dried and, in general, calcined. Phosphoric acid can also be sprayed onto the carrier in an impregnating mill.

The catalysts described here may be employed alternatively as 2-4 mm extrudates, as tablets of 3-5 mm diameter, as powders having particles sizes of from 0.1 to 0.5 mm or as fluidizable catalysts.

Palladium catalysts are suitable for the Rosenmund reduction used according to the invention, the palladium being applied to different carriers, e.g. active carbon, zeolites, silicas, aluminas, titanium oxides or zirconium dioxides, and tertiary amine bases, such as tert-butylamine, pyridine, quinoline and chalcogenides such as sulfur, selenium or tellurium being added.

The reaction conditions generally chosen for the novel conversion of the epoxides or glycols comprise a temperature of from 200° to 500° C., preferably from 200° to 400° C., and a WHSV of from 0.1 to 20, preferably from 0.5 to 5, $h^{-1}$ (g of epoxides per g of catalyst per hour) in the gas phase, which is preferred. In general, the conversion increases sharply with increasing temperature, whereas the selectivity decreases only slightly in a particular temperature range.

It is also possible to carry out the reaction in the liquid phase (suspension, trickle-bed or liquid-phase procedure).

As a rule, the process is carried out under atmospheric pressure or, depending on the volatility of the starting compound, under reduced or superatmospheric pressure, a continuous procedure being preferred.

Sparingly volatile or solid educts are used in dissolved form, for example in solution in tetrahydrofuran, toluene or petroleum ether. In general, dilution with solvents such as those mentioned above is also possible.

The Rosenmund reduction is carried out in the liquid phase at from 0° to 130° C., preferably from 25° to 100° C. The reaction is generally effected in solution, hydrocarbons, preferably toluene, xylene, benzene, ethylbenzene or diethylbenzene, being used as solvents. The procedure for the Rosenmund reduction is, for example, as follows.

The carbonyl chloride is dissolved in an inert solvent, for example xylene, and hydrogenation in the presence of a palladium catalyst. The hydrogen chloride eliminated escapes in gaseous form from the reaction mixture or, when sodium acetate or a tertiary organic base is present, is bound. The catalyst and, where relevant, sodium chloride or the hydrochloride of the tertiary organic base are filtered off, after which the aldehyde is obtained by distilling the filtrate.

However, the filtrate may also be used directly in a subsequent reaction, for example acetalation, i.e. without isolating the aldehyde.

After the reaction, the phenylacetaldehydes formed are isolated from the reaction mixture by a conventional technique, e.g. distillation; unconverted educts are, if necessary, recycled to the reaction according to the invention. Because of the very high yields, the reaction products can be further processed directly. In the process according to the invention, the monomeric compounds are preferentially formed. However, if oligomers, e.g. trimeric phenylacetaldehydes, are also formed, they can be separated off and cleaved to give the desired monomers by a conventional method.

The compounds obtainable by the novel process are important intermediates for biologically active compounds, e.g. insecticides such as resmethrin. For example, they can also readily be further processed to give amines, alcohols and acids by methods familiar to the skilled worker, for example by oxidation with oxygen or by reduction, e.g. catalytic hydrogenation or hydrogenation under aminating conditions. The said products are in turn useful intermediates.

Compounds unknown to date can be prepared by the novel process. These compounds together with their characteristic physical or spectroscopic data are listed in Table 8. The compounds which are already known are shown in Table 9.

The epoxides can be prepared either by epoxidation of the corresponding styrenes or by hydrogenation of haloacetophenones to chlorohydrins or bromohydrins followed by cyclization in an alkaline medium. By reacting the epoxides with water, alcohols, carboxylic acids or phenols, it is possible to prepare further intermediates, which can be subjected to a rearrangement reaction to give phenylacetaldehydes.

The Examples which follow illustrate the invention.

EXAMPLES 1 TO 33

The reactions are carried out under isothermal conditions in a tube reactor (0.6 cm coil, 90 cm long) in the gas phase for not less than 6 hours. Separation and characterization of the reaction products are effected by conventional methods. Quantitative determination of the reaction products and of the starting materials is effected by gas chromatography and the CO number.

The catalysts used in the Examples for converting epoxides and glycols to phenylacetaldehydes are:

Catalyst A (according to the invention)

The aluminosilicate zeolite of the pentasil type is prepared under hydrothermal conditions, under autogenous pressure at 150° C., from 650 g of finely divided $SiO_2$ and 203 g of $Al_2(SO_4)_3$ . 18 $H_2O$ in 10 kg of an aqueous 1,6-hexanediamine solution (weight ratio of mixture 50:50) in a stirred autoclave. The crystalline reaction product is filtered off, washed thoroughly, dried at 110° C. for 24 hours and then calcined at 500° C. for 24 hours. This aluminosilicate zeolite contains 92.8% by weight of $SiO_2$ and 4.2% by weight of $Al_2O_3$.

Catalyst A is obtained by molding the pure aluminosilicate zeolite of the pentasil type with molding assistants to give 2 mm extrudates and drying the latter at 110° C. for 16 hours and calcining them at 500° C. for 24 hours.

Catalyst B (according to the invention)

The borosilicate zeolite of the pentasil type is prepared in a hydrothermal synthesis from 640 g of finely divided $SiO_2$, 122 g of $H_3BO_3$ and 8 kg of an aqueous 1,6-hexanediamine solution (weight ratio of the mixture 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$.

This material is molded with molding assistants to prepare 2 mm extrudates, which are dried at 110° C. for 16 hours and calcined at 500° C. for 24 hours.

Catalyst C (according to the invention)

Catalyst C is prepared by doping catalyst B with Cs₂CO₃, drying the product at 130° C. for 2 hours and calcining it at 540° C. for 2 hours. The Cs content is 1.3% by weight.

Catalyst D (according to the invention)

Catalyst D is prepared from a commercially available mordenite (Zeolon 900 H ®), ion exchange with 20% strength ammonium chloride being carried out in order to reduce the residual sodium content to 0.025% by weight or lower (Na value after drying at 110° C. and calcination at 500° C.).

Catalyst E (according to the invention)

In the preparation of catalyst E, a commercially available erionite/chabazite mixture (Zeolon 500 ®) is subjected to ion exchange with 20% strength ammonium chloride solution until the material calcined at 500° C. has a residual sodium content of 0.11% by weight or lower.

Catalyst F (according to the invention)

A commercially available L zeolite (Baylith L ®) is molded with boehmite in a weight ratio of 80:20 to give 2 mm extrudates. Drying at 110° C. for 16 hours and calcination at 500° C. for 16 hours gives the ready-prepared catalyst F.

Catalyst G (comparative catalyst)

Catalyst G is obtained by subjecting commercially available chinopthilolite (Zeolon 400 ®) to ion exchange with 20% strength ammonium chloride solution until the product calcined at 500° C. has a residual sodium content of 0.13% by weight or lower.

Catalyst H (comparative catalyst)

Commercially available NaY zeolite is extruded with boehmite in a weight ratio of 60:40, and the extrudates are dried at 110° C., calcined at 500° C. for 16 hours and subjected to ion exchange with 20% strength ammonium chloride solution. The residual sodium content of catalyst H is 0.2% by weight (after calcination at 500° C.), or lower.

Catalyst I (comparative catalyst)

Boehmite is molded with molding assistants to give 2 mm extrudates, which are dried at 110° C. for 16 hours and calcined at 500° C. for 16 hours.

Catalyst J (comparative catalyst)

Hydrated niobium oxide is molded with finely divided $SiO_2$ in a weight ratio of 70:30 to give 2 mm extrudates, which are dried at 110° C. and calcined at 300° C. for 2 hours.

Catalyst K (comparative catalyst)

Hydrated niobium oxide is molded with finely divided $SiO_2$ in a weight ratio of 80:20 to give 2 mm extrudates, which are dried at 110° C. and calcined at 500° C. for 16 hours.

Catalyst L (comparative catalyst)

Catalyst L is a precipitated aluminum phosphate obtained by precipitation from $Al(NO_3)_3/H_3PO_4$ solution with $NH_3$ at pH 6-7. The precipitate is filtered off, dried at 110° C. and calcined at 500° C. Catalyst L contains 28.5% by weight of Al and 13.2% by weight of P.

Catalyst M (according to the invention)

$AlPO_4$-9 (APO-9) is synthesised by dissolving or suspending 98% pure phosphoric acid and 136 g of boehmite, respectively, in 400 g of water, adding an aqueous solution of 112 g of diazabicyclo[2.2.2]octane (DABCO) and 320 g of $H_2O$ and reacting this mixture in a stirred autoclave at 200° C. for 336 hours under autogenous pressure. The crystalline material is filtered off, dried at 120° C. and calcined at 500° C. for 16 hours. The $AlPO_4$-9 synthesised in this manner contains 49.0% by weight of $P_2O_5$ and 37.1% by weight of $Al_2O_3$. This material is molded with extrudation assistants to give 3 mm extrudates, which are dried repeatedly at 120° C. and calcined at 500° C. for 6 hours.

Catalyst N (according to the invention)

$AlPO_4$-21 (APO-21) is synthesised by stirring together 200 g of 98% pure phosphoric acid, 156 g of precipitated aluminum hydroxide and 71 g of pyrrolidone in 900 g of water and then carrying out the reaction at 200° C. under autogenous pressure in the course of 91 hours. The product dried at 120° C. and calcined at 500° C. contains 56.6% by weight of $P_2O_5$ at 43.4% by weight of $Al_2O_3$. This $AlPO_4$-21 is molded with extrudation assistants to give 2 mm extrudates, which are dried at 110° C. and calcined at 500° C. for 16 hours.

Catalyst O (according to the invention)

$AlPO_4$-5 (SAPO-5) is prepared from a mixture of 200 g of 98% pure phosphoric acid, 136 g of boehmite, 60 g of silica sol (30% strength), 287 g of tripropylamine and 587 g of $H_2O$. This mixture is reacted at 150° C. for 168 hours under autogenous pressure. The crystalline product is filtered off, dried at 120° C. and calcined at 500° C. SAPO-5, which contains 49.8% by weight of $P_2O_5$, 33.0% by weight of $Al_2O_3$ and 6.2% by weight of $SiO_2$, is molded with an extrudation assistant to give 3 mm extrudates, which are dried at 120° C. and calcined at 500° C.

Catalyst P (according to the invention)

$AlPO_4$-11 (SAPO-11) is synthesised from a mixture of 200 g of $H_3PO_4$, 136 g of $AlOOH$, 60 g of silica sol (30% strength), 91 g of dipropylamine and 890 g of water. The reaction is carried out at 200° C. in the course of 96 hours under autogenous pressure. The mixture is filtered, and the product is dried at 120° C. and calcined at 500° C. SAPO-11 contains 457.7% by weight of $P_2O_5$, 39.4% by weight of $Al_2O_3$ and 6.4% by weight of $SiO_2$. This crystalline product is molded with an extrudation assistant to give 3 mm extrudates, which are dried at 120° C. and calcined at 500° C. for 16 hours.

Catalyst Q (according to the invention)

$BPO_4$ is prepared by combining 49 g of $H_3BO_3$ and 117 g of $H_3PO_4$ (75% strength) in a kneader, evaporating off excess water and molding the reaction product to give 3 mm extrudates. The latter are dried at 100° C. and calcined at 350° C. Catalyst Q contains 8.77% by weight of B and 28.3% by weight of P.

Catalyst R (according to the invention)

$CePO_4$ is obtained from 52 g of $Ce(NO_3)_3 \cdot 6H_2O$ and 56 g of $NaH_2PO_4 \cdot 2H_2O$, by precipitation. The material is filtered off and converted to extrudates, which are dried at 120° C. and calcined at 450° C. Catalyst R contains 47.1% by weight of Ce and 12.7% by weight of P.

Catalyst S (according to the invention)

Pumice is impregnated with $H_3PO_4$ (75% strength), dried at 120° C. and calcined at 450° C. The $H_3PO_4$ content of catalyst S is 5% by weight.

Catalyst T (comparative catalyst)

Tonsil AC ® (bentonite).

Catalyst U (according to the invention)

$SiO_2$ (D 11-11 ®) is impregnated with $NaH_2PO_4 \cdot 2H_2O$, dried at 120° C. and calcined at 400° C.

Catalyst V (according to the invention)

Catalyst D 11-11 ®) is impregnated with $H_3BO_3$ dissolved in $CH_3OH$, and is dried at 120° C. and calcined at 500° C. for 15 hours. Boron content is 3.0% by weight ($B_2O_3$).

Catalyst W (according to the invention)

KC Trockenperlen WS ® containing about 97% SiO$_2$ and about 3% of Al$_2$O$_3$ are impregnated with H$_3$BO$_3$ dissolved in CH$_3$OH, and are dried at 110° C. and calcined at 500° C. for 5 hours. The boron content is 15.7% by weight (B$_2$O$_3$).

Catalyst X (comparative catalyst)

TiO$_2$ P$_{25}$ ® is molded with extrudation assistants to give 2 mm extrudates, which are dried at 110° C. and calcined at 500° C. for 16 hours.

Catalyst Y (comparative catalyst)

ZnO R5-10 ®

The experimental results obtained with these catalysts are summarized in Tables 1 to 6.

EXAMPLES 1 TO 6

Examples 1 to 5 (Table 1) illustrate the temperature dependence of the conversion of styrene oxide to phenylacetaldehyde. Example 6 (Table 1) is a comparative example. It can also be seen here that the novel zeolites suppress the formation of trimeric phenylacetaldehyde.

EXAMPLES 7 TO 15

Examples 7 to 13 (Table 2) illustrate the isomerization of styrene oxide to phenylacetaldehyde over various novel zeolite catalysts. In Examples 14 and 15 (Table 2), the same reaction is carried out over comparative zeolite catalysts.

These Examples show that not every zeolite catalyst is equally suitable for the process according to the invention.

EXAMPLES 16 TO 24

In Examples 16 to 23 (Table 3), the rearrangement reaction is carried out over non-zeolite catalysts based on niobium oxide, precipitated and hydrothermally prepared aluminum phosphates, silicon aluminum phosphates and boron phosphates. Examples 18 and 24 show that not every phosphate (Table 3) is equally suitable for the rearrangement, and Examples 16 and 17 that not every metal oxide (Table 3) is equally suitable for the rearrangement.

EXAMPLES 25 TO 30

Examples 25 to 30 illustrate the rearrangement of styrene oxide to give phenylacetaldehyde over carriers impregnated with H$_3$PO$_4$ or H$_3$BO$_3$ and over pure carriers (Table 4). Not every acidic oxide is suitable for the rearrangement (also see Table 1 with catalyst I).

EXAMPLES 31 TO 40

Examples 31 to 40 (Table 5) show the experimental results for the conversion of styrene oxides substituted in the aromatic nucleus to the corresponding phenylacetaldehydes.

EXAMPLE 41

Example 41 describes a catalyst life test for catalysts A and B. A quartz glass furnace having a capacity of 200 ml and an internal diameter of 25 mm is charged with catalyst A or B. This catalyst life test also demonstrates the flexibility of catalysts A and B with regard to various starting materials, which are converted one after the other with high yield, without intermediate regeneration of the catalyst. The results are shown in Tables 6a and 6b.

EXAMPLES 42 to 51

These Examples illustrate the conversion of phenylglycol, phenylglycol monomethyl ether, phenylglycol monophenyl ether or phenylglycol monoacetate to phenylacetaldehyde over catalysts A and B (Table 7).

EXAMPLE 52

Example 52 describes the preparation of 4-chlorophenylacetaldehyde.

A mixture consisting of 90 parts of 4-chlorophenylacetyl chloride, 360 parts of xylene and 4 parts of a palladium catalyst (10% of Pd on carbon) poisoned with quinoline/sulfur is gassed with 25 l/g of hydrogen at 100° C. for 1.5 hours.

The exit gas is passed into water, and the hydrogen chloride which goes into solution during this procedure is neutralized with sodium hydroxide solution. From the consumption of sodium hydroxide solution, the conversion is calculated as 98.4%.

The content of 4-chlorophenylacetaldehyde in the filtered reaction mixture (430 parts) is determined as 15.4% from the CO number and by means of gas chromatography. This corresponds to a yield of 92% of theory.

EXAMPLE 53

The preparation of 2-chloro-6-fluorophenylacetaldehyde is described here.

If the procedure described in Example 52 is followed but 90 parts of 2-chloro-6-fluorophenylacetyl chloride are used, 435 parts of reaction solution containing 14.8% of 2-chloro-6-fluorophenylacetaldehyde (determined from CO number and gas chromatogram) are obtained. The yield is thus 86% of theory. Conversion is 98.3%, determined from the amount of sodium hydroxide solution consumed by the exit gas.

EXAMPLE 54

The preparation of 3-(trifluoromethylphenyl)-acetaldehyde by the Rosenmund reduction is described in Example 54.

If the procedure described in Example 52 is followed, but 90 parts of 3-(trifluoromethylphenyl)-acetyl chloride are used, 432 parts of reaction solution containing 15.6% of 3-(trifluoromethylphenyl)-acetaldehyde (determined from the CO number and gas chromatogram) are obtained. The yield is thus 89% of theory. The conversion is 99%, determined from the amount of sodium hydroxide solution consumed by the exit gas.

TABLE 1

| | Styrene oxide to phenylacetaldehyde | | | | | |
|---|---|---|---|---|---|---|
| Example | 1 | 2 | 3 | 4 | 5 | 6*) |
| Catalyst | A | A | A | A | A | I |
| Temperature | 200° C. | 250° C. | 300° C. | 350° C. | 400° C. | 300° C. |
| WHSV | 3.0 h$^{-1}$ | 3.0 h$^{-1}$ | 3.1 h$^{-1}$ | 3.4 h$^{-1}$ | 3.2 h$^{-1}$ | 12.7 h$^{-1}$ |
| Conversion % | 100 | 100 | 100 | 100 | 100 | 100 |
| Selectivity | | | | | | |
| Product 1[1)] | 90.1 | 94.5 | 98.0 | 94.8 | 92.3 | 68.9 |
| Product 2[2)] | 7.6 | 4.3 | 1.5 | 3.4 | 3.1 | 17.0 |
| Life | 6 h | 6 h | 102 h[3)] | 54 h[3)] | 6 h | 6 h |

*[1)]comparative example
[1)]phenylacetaldehyde
[2)]trimeric phenylacetaldehyde
[3)]no deactivation detectable

TABLE 2

Styrene oxide to phenylacetaldehyde (I) over zeolite catalysts

| Example | 8 | 9 | 10 | 11 | 12 | 13 | 14*) | 15*) |
|---|---|---|---|---|---|---|---|---|
| Catalyst | A | B | C | D | E | F | G | H |
| Temperature | 300° C. | 300° C. | 300° C. | 300° C. | 300° C. | 300° C. | 300° C. | 300° C. |
| WHSV | 3.1 h$^{-1}$ | 3.0 h$^{-1}$ | 2.1 h$^{-1}$ | 2.2 h$^{-1}$ | 2.2 h$^{-1}$ | 2.2 h$^{-1}$ | 2.2 h$^{-1}$ | 2.3 h$^{-1}$ |
| Conversion % | 100 | 100 | 100 | 100 | 100 | 100 | 100 | 100 |
| Selectivity % | | | | | | | | |
| I | 99.5 | 96.9 | 98.0 | 92.8 | 93.6 | 91.4 | 85.8 | 81.3 |
| Life | 6 h | 6 h | 6 h | 6 h | 6 h | 6 h | 6 h | 6 h |

*)comparative examples

TABLE 3

Styrene oxide to phenylacetaldehyde (I) over non-zeolite catalysts

| Example | 16*) | 17*) | 18*) | 19 | 20 | 21 | 22 | 23 | 24*) |
|---|---|---|---|---|---|---|---|---|---|
| Catalyst | J | K | L | M | N | O | P | Q | R |
| Temperature | 300° C. | 300° C. | 300° C. | 300° C. | 300° C. | 300° C. | 300° C. | 300° C. | 300° C. |
| WHSV | 2.7 h$^{-1}$ | 2.5 h$^{-1}$ | 2.2 h$^{-1}$ | 2.4 h$^{-1}$ | 1.8 h$^{-1}$ | 2.4 h$^{-1}$ | 2.4 h$^{-1}$ | 2.2 h$^{-1}$ | 2.2 h$^{-1}$ |
| Conversion % | 100 | 100 | 100 | 100 | 100 | 100 | 100 | 100 | 100 |
| Selectivity % | | | | | | | | | |
| I | 82.5 | 82.0 | 84.1 | 92.7 | 89.5 | 92.5 | 89.7 | 97.9 | 79.8 |
| Life | 6 h | 6 h | 6 h | 6 h | 6 h | 6 h | 6 h | 6 h | 6 h |

*)comparative example

TABLE 4

Rearrangement of styrene oxide to phenylacetaldehyde over non-zeolite catalysts

| Example | 25*) | 26 | 27 | 28 | 29*) | 30*) |
|---|---|---|---|---|---|---|
| Catalyst | T | U | V | W | X | Y |
| Temperature | 300° C. | 300° C. | 300° C. | 300° C. | 300° C. | 300° C. |
| WHSV | 2.1 h$^{-1}$ | 2.4 h$^{-1}$ | 2.4 h$^{-1}$ | 2.4 h$^{-1}$ | 2.2 h$^{-1}$ | 2.2 h$^{-1}$ |
| Conversion % | 91.2 | 100 | 100 | 100 | 98.0 | 83.1 |
| Selectivity % | | | | | | |
| I | 89.3 | 94.5 | 95.4 | 96.4 | 74.2 | 79.1 |
| Life | 6 h | 6 h | 6 h | 6 h | 6 h | 6 h |

*)comparative example

TABLE 5

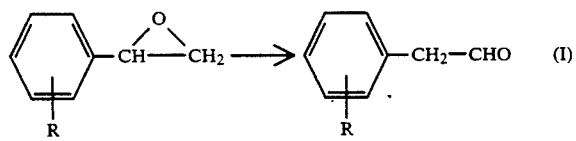

(I)

| | Example | | | | | | | | | |
|---|---|---|---|---|---|---|---|---|---|---|
| | 31 | 32 | 33 | 34 | 35 | 36 | 37 | 38 | 39 | 40 |
| Catalyst | A | A | A | A | B | A | A | A | B | Q |
| R | 4-fluoro | 2,4-Di-fluoro | 3,4-Di-fluoro | 2,4-Di-chloro | 2,4-Di-[2] chloro | 3,4-Di-[1] chloro | 4-Tri-[1] fluoromethyl | 2-Me-[2] thyl | 2-Me-[2] thyl | 2-Me-[2] thyl |
| Temperature | 300° C. | 300° C. | 250° C. | 300° C. | 300° C. | 300° C. | 300° C. | 300° C. | 300° C. | 300° C. |
| WHSV | 2.8 h$^{-1}$ | 2.9 h$^{-1}$ | 2.5 h$^{-1}$ | 3.1 h$^{-1}$ | 3.0 h$^{-1}$ | 3.0 h$^{-1}$ | 3.0 h$^{-1}$ | 2.5 h$^{-1}$ | 2.5 h$^{-1}$ | 2.5 h$^{-1}$ |
| Conversion % | 100 | 100 | 100 | 100 | 100 | 100 | 100 | 100 | 100 | 100 |
| Selectivity % | | | | | | | | | | |
| I | 93.6 | 85.2 | 82.0 | 84.9 | 89.0 | 91.5 | 94.0 | 92.5 | 92.9 | 92.1 |
| Life | 6 h | 6 h | 6 h | 6 h | 6 h | 6 h | 6 h | 6 h | 6 h | 6 h |

[1]dissolved in toluene; 50% strength solution
[2]dissolved in tetrahydrofuran; 50% strength solution

TABLE 6a

Example 41: Catalyst life test with aluminosilicate zeolite of the pentasil type (catalyst A) with various starting materials; no intermediate regeneration

| Starting materials | Styrene oxide | — | — | — | — | 4-Fluoro-styrene oxide | — | Compound II[3] | Compound III[3] | Styrene oxide |
|---|---|---|---|---|---|---|---|---|---|---|
| Total life | 17 h | 32 h | 52 h | 62 h | 77 h | 87 h | 97 h | 110 h | 115 h | 122 h |
| Time-on-stream | 17 h | 32 h | 52 h | 62 h | 77 h | 10 h | 20 h | 3 h | 3 h | 5 h |
| Temperature | 300° C. | 300° C. | 300° C. | 300° C. | 300° C. | 300° C. | 300° C. | 300° C. | 300° C. | 300° C. |
| WHSV | 0.2 h$^{-1}$ | 0.2 h$^{-1}$ | 0.2 h$^{-1}$ | 0.2 h$^{-1}$ | 0.2 h$^{-1}$ | 0.2 h$^{-1}$ | 0.2 h$^{-1}$ | 0.2 h$^{-1}$ | 0.2 h$^{-1}$ | 0.2 h$^{-1}$ |
| Conversion % | 100 | 100 | 100 | 100 | 100 | 100 | 100 | 100 | 100 | 100 |
| Selectivity % | | | | | | | | | | |
| Product[1] | 97.1 | 98.3 | 98.5 | 98.8 | 97.9 | 91.8 | 89.6 | 95.2 | 90.7 | 94.5 |

TABLE 6a-continued

Example 41: Catalyst life test with aluminosilicate zeolite of the pentasil type (catalyst A) with various starting materials; no intermediate regeneration

| Starting materials | Styrene oxide | — | — | — | — | 4-Fluoro-styrene oxide | — | Compound II[3] | Compound III[3] | Styrene oxide |
|---|---|---|---|---|---|---|---|---|---|---|
| Product[2] | 97.5 | 98.0 | 98.4 | 98.5 | 98.6 | 91.0 | 89.4 | / | / | 93.4 |

[1] Evaluation by gas chromatography
[2] Evaluation from CO number
[3] dissolved in toluene to give a 50% strength solution
compound II = 2-trifluoromethylstyrene oxide
compound III = 3,4-dichlorostyrene oxide

TABLE 6b

Example 41 b: Catalyst life test with borosilicate zeolite of the pentasil type (catalyst B) with various starting materials; no intermediate regeneration

| Starting materials | Styrene oxide | Styrene oxide | 4-Fluoro-styrene oxide | Styrene oxide | Compound IV | Compound IV | Styrene oxide | Compound V | Compound V |
|---|---|---|---|---|---|---|---|---|---|
| Total life | 15 h | 25 h | 35 h | 40 h | 45 h | 50 h | 55 h | 60 h | 65 h |
| Time-on-stream | 15 h | 25 h | 10 h | 5 h | 5 h | 5 h | 5 h | 5 h | 5 h |
| Temperature | 300° C. | 300° C. | 300° C. | 300° C. | 300° C. | 300° C. | 300° C. | 300° C. | 300° C. |
| WHSV | 0.4 h$^{-1}$ | 0.4 h$^{-1}$ | 0.3 h$^{-1}$ | 0.4 h$^{-1}$ | 0.3 h$^{-1}$ | 0.3 h$^{-1}$ | 0.4 h$^{-1}$ | 0.4 h$^{-1}$ | 0.4 h$^{-1}$ |
| Conversion % | 100 | 100 | 100 | 100 | 100 | 100 | 100 | 100 | 100 |
| Selectivity % | | | | | | | | | |
| Product[1] | 97.9 | 98.3 | 94.5 | 98.7 | 93.6 | 93.3 | 99.2 | 97.6 | 96.6 |
| Product[2] | 97.6 | 97.9 | 83.3[3] | 98.3 | 94.1 | 93.8 | 98.9 | 96.6 | 95.2 |

| Starting materials | Styrene oxide | Styrene oxide | Compound VI | Compound VI | Styrene oxide | Compound VII | Styrene oxide | Compound VIII | Styrene oxide |
|---|---|---|---|---|---|---|---|---|---|
| Total life | 70 h | 75 h | 80 h | 90 h | 95 h | 100 h | 120 h | 135 h | 130 h |
| Time-on-stream | 5 h | 5 h | 5 h | 10 h | 5 h | 5 h | 20 h | 5 h | 5 h |
| Temperature | 300° C. | 300° C. | 300° C. | 300° C. | 300° C. | 300° C. | 300° C. | 300° C. | 300° C. |
| WHSV | 0.4 h$^{-1}$ | 0.4 h$^{-1}$ | 0.4 h$^{-1}$ | 0.4 h$^{-1}$ | 0.4 h$^{-1}$ | 1.0 h$^{-1}$ | 0.4 h$^{-1}$ | 0.4 h$^{-1}$ | 0.4 h$^{-1}$ |
| Conversion % | 100 | 100 | 100 | 100 | 100 | 100 | 100 | 100 | 100 |
| Selectivity % | | | | | | | | | |
| Product[1] | 97.2 | 96.7 | 90.0 | 90.7 | 94.6 | 94.1 | 98.2 | 94.7 | 98.1 |
| Product[2] | 98.2 | 98.4 | 86.8[3] | 85.7[3] | 96.6 | — | 98.1 | 95.1 | 98.1 |

[1] Evaluation by gas chromatography
[2] Evaluation from CO number
[3] The difference in content of desired product determined by gas chromatography and from the CO number is due to the formaton of the trimeric product, which however can be converted to the monomer.
Compound IV = o-methyl-p-fluorostyrene oxide
Compound V = 2,4-difluorostyrene oxide
Compound VI = 3,4-difluorostyrene oxide
Compound VII = p-trifluoromethylstyrene oxide
Compound VIII = p-trifluoromethoxystyrene oxide

TABLE 7

Conversion of phenylglycol (IX), phenylglycol monoethyl ether (X), phenylglycol monophenyl ether (XI) and phenylglycol monacetate (XII) to phenylacetaldehyde (I)

| Example | 42 | 43 | 44 | 45 | 46 | 47 | 48 | 49 | 50 | 51 |
|---|---|---|---|---|---|---|---|---|---|---|
| Starting material | IX[1] | IX[1] | IX[1] | IX[1] | IX[1] | IX[1] | X | XII | XI | XI |
| Catalyst | A | A | A | B | B | B | A | A | A | B |
| Temperature | 250° C. | 300° C. | 350° C. | 250° C. | 300° C. | 350° C. | 300° C. | 300° C. | 300° C. | 300° C. |
| WHSV | 2.4 h$^{-1}$ | 2 h$^{-1}$ | 2.4 h$^{-1}$ | 2 h$^{-1}$ | 2 h$^{-1}$ | 2 h$^{-1}$ | 2 h$^{-1}$ | 1 h$^{-1}$ | 2.1 h$^{-1}$ | 3.5 h$^{-1}$ |
| Conversion % | 100 | 100 | 100 | 100 | 100 | 100 | 100 | 100 | 100 | 100 |
| Selectivity % | | | | | | | | | | |
| I | 92.0 | 96.4 | 87.6 | 93.2 | 94.4 | 92.2 | 95.1 | 94.7 | 91.9 | 96.3 |

[1] Phenylglycol dissolved in tetrahydrofuran to give a 25% strength solution

The physical and spectroscopic data of the novel substituted phenylacetaldehydes are reproduced in Table 8:

TABLE 8

| | Boiling point | H NMR data measured in CDCl$_3$ |
|---|---|---|
| 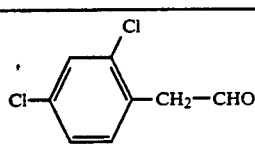 | 80° C./0.3 mbar | = 3.82 ppm (2H, —CH$_2$—)<br>7.0-7.33 ppm (2A, aromatic protons)<br>7.45 ppm (1H, aromatic protons)<br>9.75 ppm (1H, —CHO)<br>300 MHz-apparatus |

TABLE 8-continued

| Structure | Boiling point | H NMR data measured in CDCl₃ |
|---|---|---|
| 3,4-difluoro-benzyl-CHO (F at 3,4 positions, -CH₂-CHO) | 91° C./25 mbar | = 3.69 ppm (2H, —CH₂—)<br>6.87–7.21 ppm (3A, aromatic, protons)<br>9.74 ppm (1H, —CHO)<br>250 MHz-apparatus |
| 2,4-difluoro-benzyl-CHO | 93° C./30 mbar | = 3.73 ppm (2H, —CH₂—)<br>6.8–6.95 ppm (2A, aromatic, protons)<br>7.1–7.22 ppm (1H, aromatic, protons)<br>9.73 ppm (1H, —CHO)<br>250 MHz-apparatus |
| 2,4,6-trifluoro-benzyl-CHO | 81° C./13 mbar | |
| 2,4,5-trifluoro-benzyl-CHO | 56° C./1 mbar | |
| 2,3,4,5-tetrafluoro-benzyl-CHO | 87° C./23 mbar | |
| F₃C—C₆H₄—CH₂—CHO | 109° C./20 mbar | = 3.77 ppm (2H)<br>9.77 ppm (1H)<br>250 MHz-apparatus |
| F₃CO—C₆H₄—CH₂—CHO | 77–78° C./30 mbar | = 3.71 ppm (2H)<br>7.0–7.3 ppm (4H)<br>9.75 ppm (1H)<br>250 MHz-apparatus |
| F₃CS—C₆H₄—CH₂—CHO | 88–89° C./30 mbar | |
| 2-Cl, 6-F-benzyl-CHO | 102–103° C./13 mbar | |
| 4-F, 2-CH₃-C₆H₃—CH₂—C(=NOH)H | 1) | = 1.83 and 2.25 ppm (3H)<br>3.47 and 3.67 ppm (2 doublets, 1H)<br>6.73 and 7.47 ppm (2 triplets, 1H)<br>6.8 and 6.93 ppm (2H)<br>7.05 and 7.17 ppm (1H)<br>8.2 and 8.83 ppm (broad, 1H) |

TABLE 8-continued

| | Boiling point | H NMR data measured in CDCl₃ |
|---|---|---|
| [structure: 4-fluoro-2-methylphenyl-CH₂-CHO] | characterized as the oxime | |

TABLE 9

Physical and spectroscopic data of known phenylacetaldehydes prepared by one of the novel processes:

| | Boiling point | $^1$H NMR data measured in CDCl₃ |
|---|---|---|
| [structure: C₆H₅-CH₂-CHO] | 193–194° C. | |
| [structure: 4-Cl-C₆H₄-CH₂-CHO] | 100–101° C./18 mbar<br>55° C./0.1 mbar | |
| [structure: 3,4-dichlorophenyl-CH₂-CHO] | | = 3.68 ppm (2H, —CH₂—)<br>7.0–7.1 ppm (1A, aromatic, proton)<br>7.32 ppm (1H, aromatic, proton)<br>7.4–7.5 ppm (1H, aromatic, proton)<br>9.77 ppm (1H, —CHO)<br>250 MHz-apparatus |
| [structure: 4-F-C₆H₄-CH₂-CHO] | 37° C./0.25 mbar | = 3.72 ppm (2H, —CH₂—)<br>6.8–7.3 ppm (4H, aromatic, protons)<br>9.73 ppm (1H, —CHO, proton)<br>250 MHz-apparatus |
| [structure: 2-CF₃-C₆H₄-CH₂-CHO] | | = 3.93 ppm (2H, —CH₂—)<br>9.77 ppm (1H, —CHO)<br>aromatic protons cannot be assigned exactly |
| [structure: 4-H₃C-C₆H₄-CH₂-CHO] | 106–107° C./18 mbar | |
| [structure: 2-methylphenyl-CH₂-CHO] | 95° C./16 mbar | |
| [structure: 4-H₃CO-C₆H₄-CH₂-CHO] | 116–117° C./13 mbar | |

We claim:
1. A process for the preparation of a phenylacetaldehyde of the structure (I)

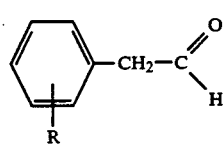

(I)

where R is hydrogen, alkyl, alkoxy, halogen, haloalkyl, haloalkoxy and/or haloalkylthio, wherein an epoxide of the structure (II)

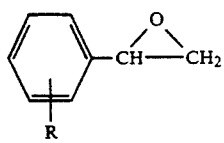

is subjected to a catalytic rearrangement reaction over a zeolite of the pentasil type, of the mordenite type, of the erionite/chabazite type or of the L type.

2. The process of claim 1, wherein an aluminosilicate zeolite of the pentasil type is used as the catalyst.

3. The process of claim 1, wherein a borosilicate zeolite of the pentasil type is used as the catalyst.

4. The process of claim 1 wherein said reaction occurs in the gas phase.

5. The process of claim 4, wherein the epoxide of the structural formula (II) is subjected to a catalytic rearrangement reaction at a temperature of from 200° to 500° C., and a WHSV of 0.1 to 20 h$^{-1}$ over a zeolite catalyst of the pentasil type, said catalyst being selected from the group consisting of aluminosilicate zeolites and borosilicate zeolites.

6. A process for the preparation of a phenylacetaldehyde of the structure (I)

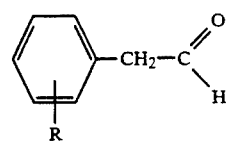

where R is hydrogen, alkyl, alkoxy, halogen, haloalkyl, haloalkoxy and/or haloalkylthio, wherein an epoxide of the structure (II)

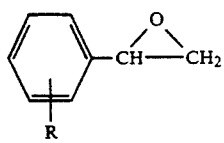

is subjected to a catalytic rearrangement reaction in the gas phase at a temperature of from 200° to 500° C. and a WHSV of 0.1 to 20 h$^{-1}$ over a zeolite catalyst of the pentasil type, said catalyst being selected from the group consisting of aluminosilicate zeolite and borosilicate zeolite.

* * * * *